(12) United States Patent
Newell

(10) Patent No.: US 6,696,269 B2
(45) Date of Patent: Feb. 24, 2004

(54) MICROBIOLOGICAL TESTING METHOD AND RELATED APPARATUS WITH DIFFUSE-WHITE LIGHT EMITTING DIODES

(75) Inventor: Vance Alan Newell, Santa Barbara, CA (US)

(73) Assignee: Giles Scientific, Inc., Santa Barbara, CA (US)

( * ) Notice: Subject to any disclaimer, the term of this patent is extended or adjusted under 35 U.S.C. 154(b) by 82 days.

(21) Appl. No.: 10/112,930

(22) Filed: Mar. 28, 2002

(65) Prior Publication Data

US 2003/0186350 A1 Oct. 2, 2003

(51) Int. Cl.[7] .............................. C12Q 1/18; C12Q 1/00; G01N 33/53; C12M 1/00
(52) U.S. Cl. ......................... 435/32; 435/283.1; 435/4; 435/968
(58) Field of Search ................................ 435/32, 283.1, 435/4, 968

(56) References Cited

U.S. PATENT DOCUMENTS

| 5,465,114 A | * | 11/1995 | Miyamoto | .................... 358/93 |
| 5,500,188 A | * | 3/1996 | Hafeman et al. | ......... 422/82.02 |
| 5,976,892 A | * | 11/1999 | Bisconte | .................... 436/172 |

\* cited by examiner

*Primary Examiner*—Louise N. Leary
(74) *Attorney, Agent, or Firm*—R. Neil Sudol; Henry Coleman; William Sapone

(57) ABSTRACT

An apparatus for use in carrying out a microbiological assay on samples in a petri plate has a support for holding the petri plate, a camera, and a plurality of diffuse-white-light emitting diodes. The camera optically detects microbe-growth inhibition zones arising about the diffusion disks and is disposed above the support. The diodes are disposed in a circular array above the support and below the camera for illuminating the nutrient medium and the drug diffusion disks. An electrical power and control circuit energizes the diodes with power from the computer upon an activation of the camera.

27 Claims, 1 Drawing Sheet

MICROBIOLOGICAL TESTING METHOD AND RELATED APPARATUS WITH DIFFUSE-WHITE LIGHT EMITTING DIODES

BACKGROUND OF THE INVENTION

The present invention relates to a microbiological testing apparatus and an associated method. More specifically, the present invention relates to an apparatus for use in the automated antibiotic susceptibility testing of samples, such as those from patients possibly infected by a microorganism.

Agar disk diffusion is a widely recognized microbiological assay for measuring susceptibility—a parameter effectively defined by the assay itself. The susceptibility of a microorganism to a given antibiotic is essentially a description of the size of the inhibitory zone resulting from placement of a permeable disk impregnated with the given antibiotic onto an agar surface inoculated with a sample culture of the microorganism. This parameter provides a measure of the ability of the antibiotic compound to stem growth of the target culture, but it is also a complex function of diffusion constants and other kinetic factors.

Early laboratory standards for the agar diffusion assay involved qualitative evaluation by a laboratory technician, characterizing the tested bacterium's interaction with the antimicrobial agent as "susceptible", "moderately susceptible", "intermediate" or "resistant", depending on the size of the inhibition zone surrounding the antibiotic impregnated disk.

Of additional use to the clinician is a related quantitative measure of susceptibility, known as "minimum inhibitory concentration" (MIC). Although still requiring additional information to translate the parameter into a prescription for clinical practice, this quantitative measure eliminates some sources of complexity and uncertainty relative to qualitative susceptibility. An additional useful clinical parameter is the "inhibitory quotient", which expresses the ratio of the drug concentration in a particular body tissue at a lowest clinical dose to the minimum inhibitory concentration.

The MIC is ideally determined by an assay appropriately called the dilution method, which straightforwardly involves inoculating a series of test tubes with the target culture, the test tubes containing a series of dilutions of the target antibiotic. One series of test tubes therefore tests only one culture and one antibiotic, in contradistinction to an agar diffusion assay petri dish, which may test a plurality of antibiotics simultaneously with less material and expense. The advantage of the dilution method is that it provides less ambiguously interpretable quantitative results relative to the agar diffusion method, while its disadvantage is primarily its expense, both in materials and labor.

It is therefore desirable to have a device which automatically translates a dimension of an inhibition zone on an agar diffusion assay plate into a more clinically useful quantitative measure of drug-bacterium interaction, such as the MIC. Such a device is disclosed by U.S. Pat. No. 4,701,850. It is further desirable to have a device which automates the process of reading the apposite linear dimension of the inhibition zone, such devices being revealed in subsequent United States patents. The relation of the diameter of the inhibition zone to the MIC for an unknown biological agent is approximated by a linear relation, the parameters for which assumed relation for a particular antibiotic being determined by statistical estimation based on the scatter of data points whose coordinates are inhibition zone diameters and actual minimum inhibitory concentrations determined by dilution assay for a particular microorganism, the relation being assumed linear and being assumed to persist for untested organisms.

Since a number of different antibiotics are simultaneously tested against an unknown culture on a single agar plate and since these antibiotics are characterized by different values of the linear parameters relating inhibition zone dimensions to estimated MIC, and by differing values of the measured dimension of the inhibition zone in a given test, it would be advantageous to have a method of associating the zone surrounding a given antibiotic disk with the subject antibiotic compound without further operator intervention or opportunity for human error. Such a method is disclosed in U.S. Pat. No. 6,107,054.

In extant microbiological testing devices which measure the diameter of microbe inhibition zones about drug diffusion disks, illumination of the petri plate and the disks thereon is by a light source separate from the camera or other optical detection device. A switch must be manually thrown prior to image acquisition. In addition, it is desirable to de-energize the illumination afterimage acquisition.

OBJECTS OF THE INVENTION

An object of the present invention is to provide an improved apparatus and/or associated method for microbiological testing.

A further object of the present invention is to provide a microbiological testing apparatus and/or method which enables automatic determination of a susceptibility of a microorganism to an antibiotic agent.

An additional object of the present invention is to provide such a microbiological testing apparatus and/or method which is easy to use.

It is a supplemental object of the present invention to provide such a microbiological testing apparatus and/or method which is inexpensive to use.

A particular object of the present invention is to provide an essentially automated microbiological testing apparatus and/or method wherein a dimension of an inhibition zone associated with an antibiotic impregnated disk on an agar plate is measured automatically.

A more particular object of the present invention is to provide such a microbiological testing apparatus and/or method which facilitates association of a microorganism susceptibility measurement with a particular antibiotic agent.

These and other objects of the present invention will be apparent from the descriptions and illustrations provided herein.

SUMMARY OF THE INVENTION

The present invention is directed in part to an apparatus for use in carrying out a microbiological assay on samples in a petri dish. The petri dish or plate contains a nutrient medium, a plurality of drug diffusion disks each disposed on the medium and carrying an antibiotic agent, and a microbial solution deposited on the medium. The apparatus of the present invention comprises a support for holding the petri plate, an optical monitoring device, and a plurality of light emitting diodes. The optical monitoring device optically detects microbe-growth inhibition zones arising about the diffusion disks and is disposed above the support. The optical monitoring device is an imaging device such as a video camera, a digital camera, a scanner, a linear array, etc.

The diodes are disposed in an array above the support and below the optical monitoring device for illuminating the nutrient medium and the drug diffusion disks.

Preferably, the diodes are diffuse-white-light emitting diodes. This kind of diode provides a broad-spectrum illumination adequately approximating natural light. Pursuant to the invention, the number and distribution of the diodes results in a sufficient degree of illumination for purposes of determining the sizes of microbe-inhibition zones about the drug diffusion disks and also for purposes of automatically reading the antibiotic identification codes imprinted on the disks. A microbiological testing apparatus with an automated reading of antibiotic identification codes is disclosed in U.S. Pat. No. 6,107,054, the disclosure of which is hereby incorporated by reference.

In accordance with another feature of the present invention, electrical transmission components are provided for supplying electrical power to the diodes from a computer in response to an activation of the optical monitoring device. The electrical transmission components may include a relay connected at an output to the diodes, connected at a control input at least indirectly to the optical monitoring device, and connectable at a power input to the computer. Electrical power may also be provided to the optical monitoring device from the computer. In that case, an electrical lead is connected at one end to the optical monitoring device and connectable at an opposite end to the computer for supplying power from the computer to the optical monitoring device.

The optical monitoring device is typically connectable to the computer for transmitting thereto image data for processing.

In accordance with further features of the present invention, the diodes are disposed in an annular array, for instance, on an upright annular surface, while an annular light shield is disposed between the diodes and the optical monitoring device. Preferably, the annular surface is white, thereby enhancing the amount of illumination falling on the petri plate and the drug diffusion disks from the diodes.

Pursuant to another embodiment of the present invention, an apparatus for carrying out a microbiological assay comprises a support for holding a petri plate containing a nutrient medium, a plurality of drug diffusion disks each disposed on the medium and carrying an antibiotic agent, and a microbial solution deposited on the medium. The apparatus additionally comprises an optical monitoring device disposed above the support for optically detecting microbe-growth inhibition zones arising about the diffusion disks. The apparatus further comprises a plurality of diffuse-white-light emitting diodes disposed in an array above the support and below the optical monitoring device for illuminating the nutrient medium and the drug diffusion disks. The apparatus also comprises a computer connected to the optical monitoring device for receiving and processing image data therefrom, electrical transmission circuitry being operatively connected to the computer, the optical monitoring device and the diodes for transmitting power from the computer to the diodes upon an activation of the optical monitoring device.

As discussed above, the electrical transmission circuitry may include a relay connected at an output to the diodes, at a control input at least indirectly to the optical monitoring device, and at a power input to the computer. The computer is also connected to the optical monitoring device for supplying power to the optical monitoring device.

In a particular embodiment of the invention, an apparatus for carrying out a microbiological assay comprises (a) a support for holding a microbiological assay petri plate, (b) a camera disposed above the support for optically detecting microbe-growth inhibition zones arising about diffusion disks on the petri plate, (c) a plurality of diffuse-white-light emitting diodes disposed in an array above the support and below the optical monitoring device, (d) a light shield disposed between the diodes and the camera for blocking a passage of light directly from the diodes to a lens or aperture of the camera, (e) a relay or switch connected to the diodes and at least indirectly to the camera for enabling a transmission of electrical power to the diodes in response to a signal from the camera, (f) a first coupling element for enabling information transfer between the camera and a computer, and (g) a second coupling enabling power transfer from the computer to the camera and the relay.

A method for use in carrying out a microbiological assay, in accordance with the present invention, analyzes a petri plate containing a nutrient medium, a plurality of drug diffusion disks each disposed on the medium and carrying an antibiotic agent, and a microbial solution deposited on the medium. The method includes activating an optical monitoring device disposed above the petri plate for optically detecting microbe-growth inhibition zones arising about the diffusion disks, and energizing a plurality of light emitting diodes disposed in an array above the petri plate and below the optical monitoring device to illuminate the nutrient medium and the drug diffusion disks.

Preferably, the energizing of the diodes includes transmitting power from a computer to the diodes. In that event, the energizing of the diodes may be carried out automatically upon the activating of the optical monitoring device. In addition, image data is transmitted from the optical monitoring device to the computer and the computer is operated to process the image data. The energizing of the diodes may additionally include activating a relay or switch to transmit power from the computer to the diodes.

A microbiological testing apparatus with a lighting array in accordance with the present invention provides several major and novel advantages over existing lighting. First, the diodes consume very little power and thus enable one to power the illumination assembly via a PC interface, eliminating the need for a "wall/external" power supply. Second, the diodes provide an intense, broad-spectrum evenly distributed light, eliminating the need for a light diffuser and enabling good color analysis. Third, the lighting assembly is very rugged and relatively unbreakable (a problem during shipping). Fourth, the lighting assembly has an extremely long life, eliminating the need to replace it during the expected product life of 5 to 10 years. Fifth, the lightning assembly can be switched on and off automatically using the camera controls at the PC; this eliminates the requirement for external light on-off switches and/or timer switches activated by placement of test-plates. All these advantages provide improvements to performance of the image-analysis, reduce/eliminate maintenance, simplify construction and tend to reduce costs.

DETAILED DESCRIPTION OF THE PREFERRED EMBODIMENTS

Figure 1:
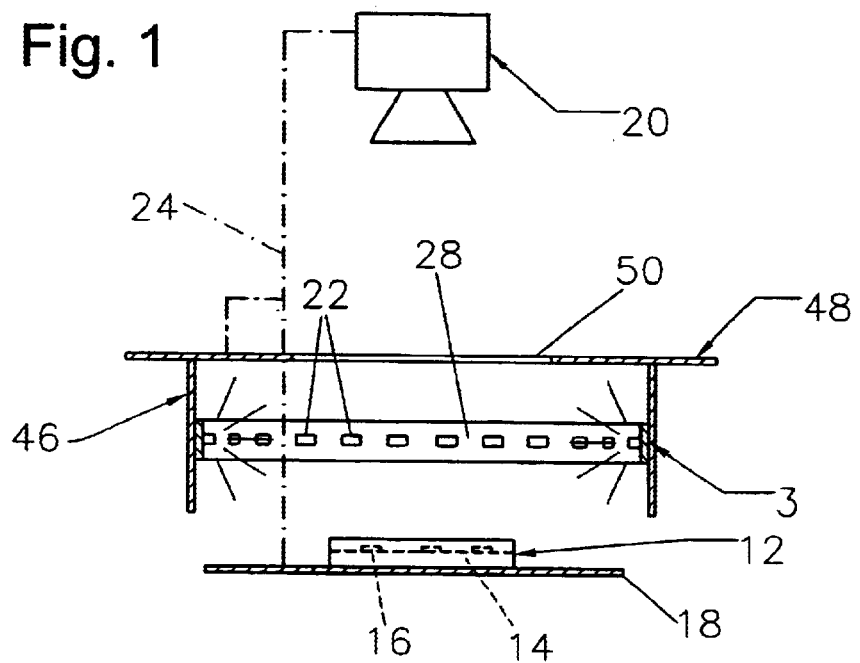
FIG. 1 is a diagram of a diffusion disk reader pursuant to the present invention.

FIG. 1 depicts a diffusion disk reader for carrying out a microbiological assay on samples in a petri dish or plate 12.

As disclosed in various prior patents and publications, including U.S. Pat. No. 6,107,054 and U.S. Pat. No. 4,701,850, the disclosures of which are hereby incorporated by reference, petri dish or plate 12 contains a nutrient medium 14, a plurality of drug diffusion disks 16 each disposed on the medium and carrying an antibiotic agent, and a microbial solution (not shown) deposited on the medium.

The disk reader includes a support 18 for holding petri plate 12 and further includes an optical monitoring device 20 and a plurality of light emitting diodes 22. Support 18, optical monitoring device 20, and diodes 22 are all mounted to a frame or casing 24.

Optical monitoring device 20 typically takes the form of a video camera or charge coupled device and is operated under the control of a computer 26 (FIG. 2) to optically detect microbe-growth inhibition zones (not shown) arising about the diffusion disks 16 and is disposed above support 18. Diodes 22 are disposed at angularly equispaced locations in a circular array above support 18 and below camera 20 for illuminating nutrient medium 14 and drug diffusion disks 16.

Diodes 22 are diffuse-white-light emitting diodes, rather than directional or focused. This kind of diode provides a broad-spectrum illumination satisfactorily approximating natural light. Diodes 22 are attached to wires (not illustrated) on a flexible plastic strip 28. Strip 28 can be provided in any length with diodes 22 spaced at any desired interval. Strip 28 is exemplarily twenty-eight inches long, while diodes 22 are spaced one inch apart.

Diodes 22 are disposed in a circular array located about three inches over petri plate 12 and are aimed horizontally. Camera 20 more particularly takes the form of a digital camera board located approximately fourteen inches above petri plate 12, or eleven inches above the array of diodes 22. It is possible to locate a second array of diodes (not shown) beneath support 12 for purposes of providing "back-lighting" for certain applications, for example, in enumerating bacterial colonies. In that case, support 18 is made of a transparent or translucent material.

Figure 2:
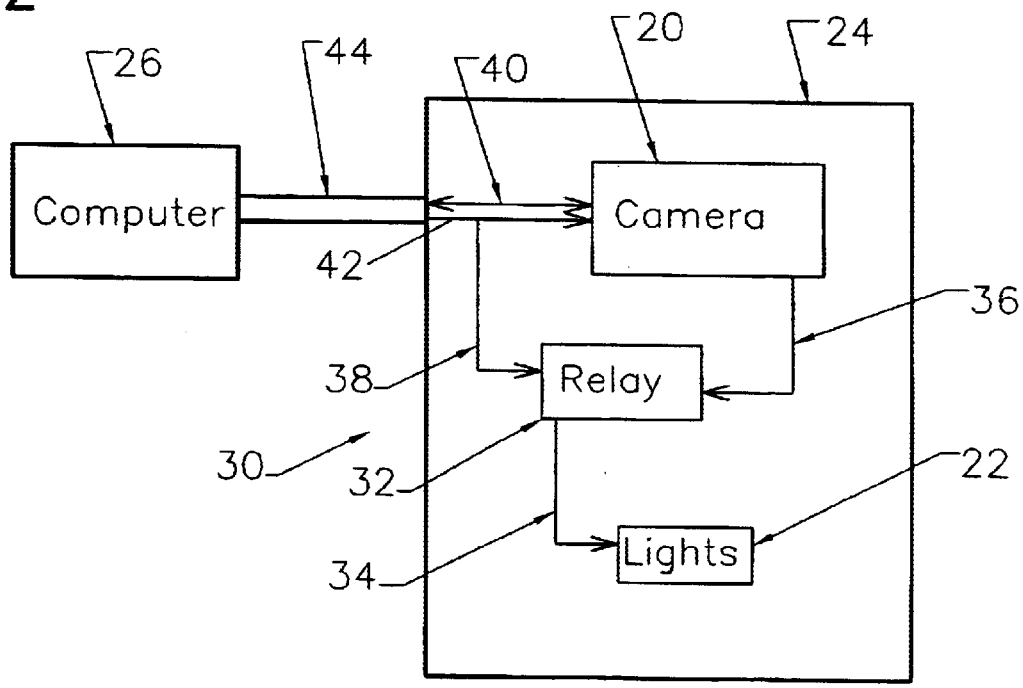
FIG. 2 is a block diagram showing electrical connections of the disk reader of FIG. 1 with a personal computer.

FIG. 2 depicts an electrical power and control circuit 30 in part transmitting electrical power to diodes 22 from computer 26 in response to an activation of camera 20. Circuit 30 includes a relay 32 connected via an output lead or leads 34 to diodes 22, connected via a control lead 36 to camera 20, and connectable at a power transmission wire 38 to computer 26. Circuit 30 additionally includes a coupling in the form of a multiple 40 operative linked to camera 20 for transmitting control signals thereto from computer 26 and for transmitting image data from the camera to the computer. A coupling or lead 42 may also be provided for carrying electrical power to camera 20 from computer 26. During use of the disk diffusion reader system of FIG. 2, power transmission wire 38, multiple 40 and lead 42 are connected to computer 26 via an IEEE 1394 Firewire cable 44.

During use of the disk diffusion reader of FIGS. 1 and 2, activation of camera 20 by computer 26 results in the generation of a control signal on lead 36. The occurrence of that control signal energizes relay 32 which then connects power transmission wire 38 to diodes 22. Diodes 22 are consequently energized to cast a diffuse illumination on nutrient medium 14 and drug diffusion disks 16. Accordingly, the energizing of diodes 22 is carried out automatically upon the activating of camera 20. Image data is transmitted from camera 20 to computer 26 via multiple 40 and cable 44. Computer 26 is programmed to process the image data to measure the sizes of microbial-growth-inhibition zones about disks 16.

Diodes 22 are disposed on an upright annular surface or panel 46, while an annular planar light shield 48 is provided between the diodes and camera 20. Preferably, the inwardly facing surface of panel 46 is white, thereby optimizing the amount of illumination falling on petri plate 12 and drug diffusion disks 16 from diodes 22.

Diodes 22 are thus powered and controlled from computer 26 via camera 20. Light shield 48 prevents light from shining directly into a lens or aperture 50 of camera 20. Shield has a circular hole 52 about five inches in diameter to allow camera 20 to take pictures (view the test plates 12 clearly). The test or petri plates 12 are generally 90–150 millimeters in diameter or 120 mm square.

The diffusion disk reader with a lighting system as described herein is for microbiology laboratory assay applications, that include but are not limited to antibiotic susceptibility tests, antibiotic potency/concentration tests, and bacterial colony enumeration. These assay plates are usually filled with nutrient medium 14 in the form of agar (a gelatinous material) that provides a clear to opaque nutrient surface for the bacteria/microorganisms to grow on.

Although the invention has been described in terms of particular embodiments and applications, one of ordinary skill in the art, in light of this teaching, can generate additional embodiments and modifications without departing from the spirit of or exceeding the scope of the claimed invention. It is to be noted, for example, that relay 32 may be operated by a control signal sent directly from computer 26 substantially simultaneously with a control signal transmitted therefrom to camera 20. It is to be noted additionally that in some applications it may be desirable to have diodes 22 manually controlled by the use of a switch either mounted external or mounted internally for actuation by a movable support or drawer 18. Alternatively, owing to their low power usage and long life, diodes 22 could remain energized whenever computer 26 is turned on. Although it is preferred to have diodes 22 powered from computer 26, it is certainly possible and within the contemplation of the present invention to have the diodes powered by a separate dedicated power supply.

Accordingly, it is to be understood that the drawings and descriptions herein are proffered by way of example to facilitate comprehension of the invention and should not be construed to limit the scope thereof.

What is claimed is:

1. An apparatus for use in carrying out a microbiological assay, comprising:
    a support for holding a petri plate containing a nutrient medium and a microbial solution deposited on said medium;
    an optical monitoring device disposed above said support; and
    a plurality of light emitting diodes disposed in an array above said support and below said optical monitoring device for illuminating said nutrient medium and drug diffusion disks.

2. The apparatus defined in claim 1, further comprising electrical transmission components for supplying electrical power to said diodes from a computer in response to an activation of said optical monitoring device.

3. The apparatus defined in claim 2 wherein said electrical transmission components include a relay connected at an output to said diodes, connected at a control input at least indirectly to said optical monitoring device, and connectable at a power input to said computer.

4. The apparatus defined in claim 3, further comprising an electrical lead connected at one end to said optical monitoring device and connectable at an opposite end to said computer for supplying power from said computer to said optical monitoring device.

5. The apparatus defined in claim 4 wherein said optical monitoring device is a camera.

6. The apparatus defined in claim 2 wherein said optical monitoring device is connectable to said computer for transmitting thereto image data for processing.

7. The apparatus defined in claim 1 wherein said array is an annular array.

8. The apparatus defined in claim 7 wherein said diodes are disposed on an upright annular surface.

9. The apparatus defined in claim 8 wherein said annular surface is white.

10. The apparatus defined in claim 7, further comprising an annular light shield disposed between said diodes and said optical monitoring device.

11. The apparatus defined in claim 1, further comprising a light shield disposed between said diodes and said optical monitoring device.

12. The apparatus defined in claim 1 wherein said diodes are diffuse-white-light emitting diodes.

13. An apparatus for carrying out a microbiological assay, comprising:

a support for holding a petri plate containing a nutrient medium and a microbial solution deposited on said medium;

an optical monitoring device disposed above said support;

a plurality of light emitting diodes disposed in an array above said support and below said optical monitoring device for illuminating said nutrient medium;

a computer connected to said optical monitoring device for receiving and processing image data therefrom; and electrical transmission circuitry operatively connected to said computer, said optical monitoring device and said diodes for transmitting power from said computer to said diodes upon an activation of said optical monitoring device.

14. The apparatus defined in claim 13 wherein said electrical transmission circuitry includes a relay connected at an output to said diodes, at a control input at least indirectly to said optical monitoring device, and at a power input to said computer.

15. The apparatus defined in claim 14 wherein said computer is connected to said optical monitoring device for supplying power to said optical monitoring device.

16. The apparatus defined in claim 15 wherein said optical monitoring device is a camera.

17. The apparatus defined in claim 13 wherein said array is an annular array.

18. The apparatus defined in claim 17 wherein said diodes are disposed on an upright annular surface.

19. The apparatus defined in claim 18 wherein said annular surface is white.

20. The apparatus defined in claim 17, further comprising an annular light shield disposed between said diodes and said optical monitoring device.

21. The apparatus defined in claim 13, further comprising a light shield disposed between said diodes and said optical monitoring device.

22. The apparatus defined in claim 13 wherein said diodes are diffuse-white-light emitting diodes.

23. An apparatus for carrying out a microbiological assay, comprising:

a support for holding a petri plate containing a nutrient medium and a microbial solution deposited on said medium;

a camera disposed above said support;

a plurality of diffuse-white-light emitting diodes disposed in an array above said support and below said optical monitoring device;

a light shield disposed between said diodes and said camera for blocking a passage of light directly from said diodes to an aperture of said camera;

a relay or switch connected to said diodes and at least indirectly to said camera for enabling a transmission of electrical power to said diodes in response to a signal from said camera;

a first coupling element for enabling information transfer between said camera and a computer; and a second coupling enabling power transfer from said computer to said camera and said relay.

24. A method for use in carrying out a microbiological assay, comprising:

providing a petri plate containing a nutrient medium and a microbial solution deposited on said medium;

activating an optical monitoring device disposed above said petri plate; and energizing a plurality of diffuse-white-light emitting diodes disposed in a predetermined array above said petri plate and below said optical monitoring device to illuminate said nutrient medium.

25. The method defined in claim 24 wherein the energizing of said diodes includes transmitting power from a computer to said diodes, further comprising transmitting image data from said optical monitoring device to said computer and operating said computer to process said image data.

26. The method defined in claim 25 wherein the energizing of said diodes is carried out automatically upon the activating of said optical monitoring device.

27. The method defined in claim 26 wherein the energizing of said diodes further includes activating a relay or switch to transmit power from said computer to said diodes.

* * * * *